United States Patent
Dadu et al.

(10) Patent No.: US 9,078,766 B2
(45) Date of Patent: Jul. 14, 2015

(54) DEVICE AND METHOD WITH POWER EFFICIENT LOCATION NOTIFICATION FUNCTION BY PERIODICALLY DEACTIVATING SIGNAL-BASED LOCATION SERVICE DURING TRAVEL UNTIL A WAKE TRIGGER CONDITION IS MET

(75) Inventors: Saurabh Dadu, Tigard, OR (US); Gyan Prakash, Beaverton, OR (US); Nagasubramanian Gurumoorthy, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 245 days.

(21) Appl. No.: 13/543,216

(22) Filed: Jul. 6, 2012

(65) Prior Publication Data

US 2014/0013136 A1    Jan. 9, 2014

(51) Int. Cl.
| | | |
|---|---|---|
| G06F 1/00 | (2006.01) | |
| A61F 2/44 | (2006.01) | |
| G06F 1/32 | (2006.01) | |
| H04W 4/02 | (2009.01) | |
| H04W 4/00 | (2009.01) | |
| H04W 64/00 | (2009.01) | |
| H04W 48/04 | (2009.01) | |
| H04M 1/725 | (2006.01) | |
| A61B 17/02 | (2006.01) | |
| A61B 17/00 | (2006.01) | |
| A61F 2/30 | (2006.01) | |

(52) U.S. Cl.
CPC .............. *A61F 2/4455* (2013.01); *A61B 17/025* (2013.01); *G06F 1/3206* (2013.01); *G06F 1/3209* (2013.01); *H04M 1/72569* (2013.01); *H04W 4/001* (2013.01); *H04W 4/02* (2013.01); *H04W 48/04* (2013.01); *H04W 64/00* (2013.01); *A61B 2017/00261* (2013.01); *A61B 2017/0256* (2013.01); *A61F 2002/30579* (2013.01); *A61F 2002/4475* (2013.01)

(58) Field of Classification Search
None
See application file for complete search history.

(56) References Cited

U.S. PATENT DOCUMENTS

| | | | |
|---|---|---|---|
| 2010/0167792 A1* | 7/2010 | Chen et al. | ...................... 455/566 |
| 2010/0246467 A1* | 9/2010 | Song et al. | ...................... 370/312 |

(Continued)

OTHER PUBLICATIONS

International Search Report and Written Opinion received for Patent Application No. PCT/US2013/049420, mailed on Jul. 29, 2013.

*Primary Examiner* — Thomas Lee
*Assistant Examiner* — Zhipeng Wang
(74) *Attorney, Agent, or Firm* — Grossman, Tucker, Perreault & Pfleger, PLLC (57) ABSTRACT

Before a device enters a power saving mode, a location-aware application in the device may provide at least one wake trigger (and a trigger limit) to a low power monitoring module (LPMM). In power saving mode, the LPMM receives device locations from a location service module and may determine when the device location corresponds to the at least one wake trigger or trigger limit. In one embodiment, device location may only be provided to the LPMM based on a condition (e.g., timer expiration or reaching a displacement threshold as measured by sensors in the device). When device location corresponds to the trigger limit, the LPMM may notify the device (e.g., cause a transition to an active power mode) so that the location-aware application can redetermine the at least one wake trigger. The device location corresponding to the at least wake trigger may also cause the LPMM to notify the device.

26 Claims, 4 Drawing Sheets

(56) References Cited

U.S. PATENT DOCUMENTS

| | | |
|---|---|---|
| 2010/0250986 A1 | 9/2010 | Black |
| 2011/0039579 A1* | 2/2011 | Karjalainen .............. 455/456.1 |
| 2011/0250871 A1 | 10/2011 | Huang |
| 2011/0250875 A1* | 10/2011 | Huang et al. ................. 455/418 |
| 2011/0306304 A1* | 12/2011 | Forutanpour et al. ...... 455/67.11 |
| 2013/0178233 A1* | 7/2013 | McCoy et al. ............. 455/456.3 |
| 2013/0237254 A1* | 9/2013 | Papakipos et al. ......... 455/456.3 |
| 2013/0238784 A1* | 9/2013 | Teller et al. .................. 709/224 |

* cited by examiner

DEVICE AND METHOD WITH POWER EFFICIENT LOCATION NOTIFICATION FUNCTION BY PERIODICALLY DEACTIVATING SIGNAL-BASED LOCATION SERVICE DURING TRAVEL UNTIL A WAKE TRIGGER CONDITION IS MET

TECHNICAL FIELD

The present disclosure relates to electronic locating systems, and more particularly, to systems configured to provide location arrival notifications while conserving system power.

BACKGROUND

Emerging mobile devices have abilities that far exceed standard voice communications. For example, mobile devices may be equipped with one or more transceivers that are configured to facilitate the transmission and reception of information utilizing various wired and/or wireless communication mediums. The ability to efficiently communicate information including voice, text, data, multimedia, etc. allows for the introduction of new functionality into mobile devices related to, for example, interpersonal interactions (e.g., email, messaging, social media, etc.), business, productivity, gaming, shopping, etc. As a result, simple cellular handsets have evolved into powerful multipurpose mobile platforms with the ability to run a large array of applications.

Early applications were directed to baseline communication functionality such as email, messaging, news feeds, etc. However, quickly applications have become more advanced, with the ability to draw on various features in a device. For example, a shopping application may be able to communicate with remote resources accessible via a wide area network (e.g., the Internet) to determine manufacturers, specifications, pricing, availability, etc. for a particular product. In addition, if the particular product is determined to be available locally, the application may be able to access location services in the mobile device to illustrate the location of the particular product, to guide the device user to the product, etc. In this manner applications may interact with various features in a mobile device to provide desired functionality to the device user.

While the benefits are evident, applications executing on mobile devices are not without some negative repercussions. In particular, applications accessing one or more communication resources in a mobile device may cause the mobile device to consume a large amount of energy. Moreover, some applications, such as the example shopping application described, continuously access communication resources to provide location, guidance, etc. This continuous operation exacerbates the energy consumption, negatively impacting the performance of the mobile device.

BRIEF DESCRIPTION OF THE DRAWINGS

Features and advantages of various embodiments of the claimed subject matter will become apparent as the following Detailed Description proceeds, and upon reference to the Drawings, wherein like numerals designate like parts, and in which:

Although the following Detailed Description will proceed with reference being made to illustrative embodiments, many alternatives, modifications and variations thereof will be apparent to those skilled in the art.

DETAILED DESCRIPTION

This disclosure describes systems and methods for power efficient location notification. Initially, some terminology may be defined to provide clarification for the following disclosure. Two modes of device operation will be disclosed herein. In "active mode" operation, all device resources may be fully available, and thus, applications and other functionality provided by the device may also be fully operational. Even when the device is not experiencing heavy usage, active mode operation may still cause substantial power consumption just based on maintaining device resources in a ready state. "Power saving mode" is a mode of operation wherein at least some of the device resources may be powered down or in a "sleep" condition. As a result, some or all of the applications and other functionality provided by the device may be unavailable for use. Power saving mode may be invoked when, for example, the user of the device does not require device applications or other functionality and wishes to conserve power in the device. Moreover, the terms "location" and "position", as well as "locating" and "positioning," may be used interchangeably throughout the disclosure with respect to location services in the device.

In one embodiment, an example device may comprise at least a host, a location services module and a low power monitoring module (LPMM). When in the active mode, the host may allow for the execution of a location-aware application that may provide functionality based, at least in part, on an awareness of the current position of the device as provided by the location services module. The location services module may provide the device location based on, for example, signal-based positioning techniques utilizing the Global Positioning System (GPS), network estimation, etc. The location-aware application does not operate when the device is in power saving mode, and thus, may provide at least one location of interest, or "wake trigger," to the LPMM prior to the host entering the power saving mode. Wake triggers may correspond to, for example, locations that the user of the device desires to visit, locations where items desired by the user of the device may be obtained (e.g., a store), etc. The LPMM may continue to access resources in the location services module when the device is in the low power mode, and may "notify" the device (e.g., may cause the device to transition from the power saving mode to the active mode) when, for example, the LPMM determines that the device location corresponds to the at least one wake trigger (e.g., that the device is at or near at least one location of interest). Upon returning to the active mode, the location-aware application may provide additional functionality based on the arrival of the device at the at least one location of interest. In this manner, desired location-related functionality and power conservation may coexist in the device.

In the same or a different embodiment, the location-aware application may also provide a trigger limit to the LPMM. The trigger limit may indicate, for example, an area outside of which wake triggers need to be redetermined (e.g., due to the wake triggers not being within range of current location of the device). Upon determining that the device is at or near the trigger limit, the LPMM may notify the device (e.g., may cause the device to transition from the power saving mode to the active mode) to redetermine the wake triggers. After the device returns to the power saving mode, the LPMM may again monitor for locations corresponding to the wake triggers.

In the same or a different embodiment, it may also be possible for the LPMM to improve energy conservation in the device by only receiving a device location from the location resources module based on a condition being met. For example, the LPMM may receive a device location only after a location monitoring timer expires, allowing the location services module to remain inactive until needed (e.g., conserving power). In another possible configuration, sensors in or accessible to the location services module (e.g., such as motion or acceleration sensors) may be employed to determine a device displacement (e.g., the distance the device has traveled from an initial starting location). Device displacement may be determined based entirely on internally sensed device motion or acceleration, and thus, may be substantially more power efficient than signal-based location determination. For example, the LPMM may be configured to receive a device displacement from the location services module and may only receive a device location when the device displacement corresponds to a threshold distance. In this manner, the device may conserve power while it is staying in one place since signal-based positioning will not be active, and may activate signal-based positioning when it is sensed that the device has changed position. In one embodiment, the LPMM may include, for example, a microcontroller and firmware integrated in a discrete integrated circuit (IC) or a system-on-a-chip (SOC).

Figure 1:
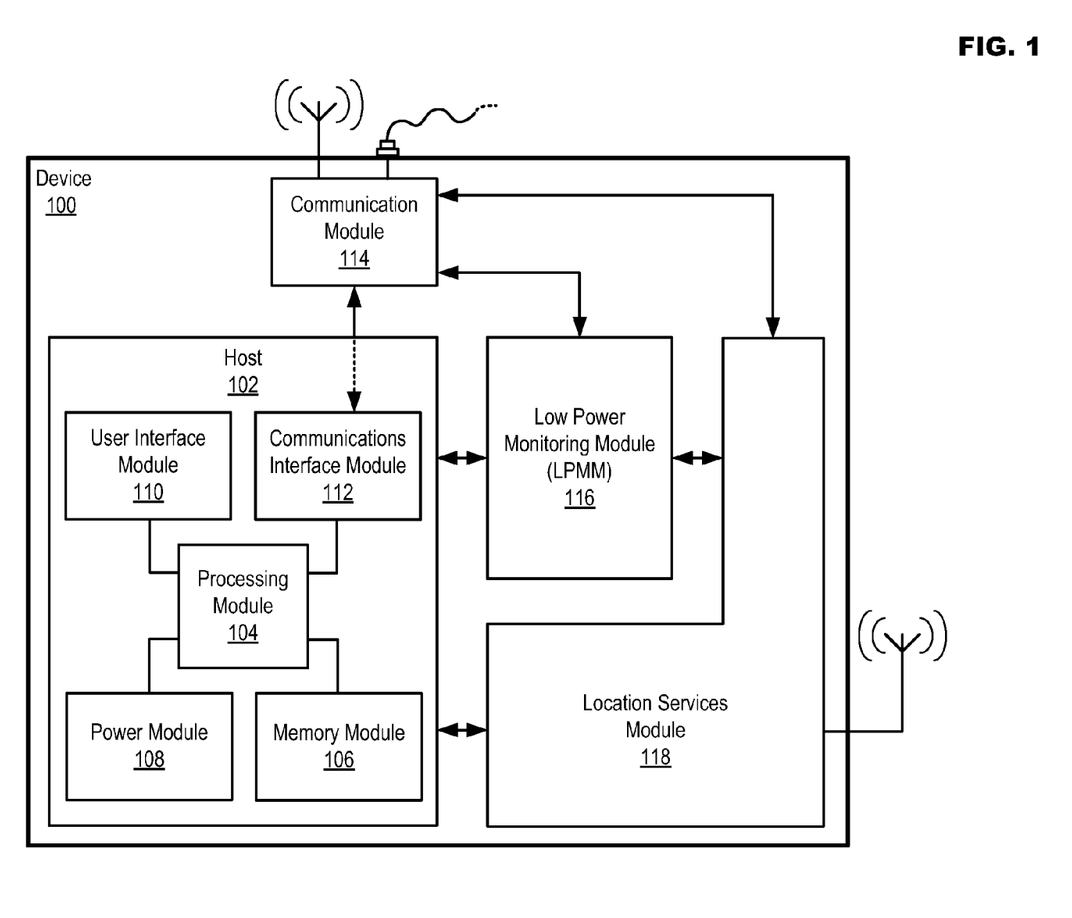
FIG. 1 illustrates an example device configured for power efficient location notification in accordance with at least one embodiment of the present disclosure.

FIG. 1 illustrates example device 100 configured for power efficient location notification in accordance with at least one embodiment of the present disclosure. Examples of device 100 may include, but are not limited to, a mobile communication device such as a cellular handset or a smartphone based on the Android® operating system (OS), iOS®, Blackberry® OS, Palm® OS, Symbian® OS, etc., a mobile computing device such as a tablet computer like an iPad®, Galaxy Tab®, Kindle Fire®, Microsoft Surface®, etc., an Ultrabook® including a low-power chipset manufactured by Intel Corporation, a netbook, a notebook computer, a laptop computer, etc. In at least one example configuration, device 100 may comprise host 102, communication module 114, low power monitoring module (LPMM) 116 and location services module 118.

Host 102 may include, for example, processing module 104, memory module 106, power module 108, user interface module 110 and communications interface module 112, which may be configured to interact with communication module 114. For example, processing module 104 may comprise one or more processors situated in separate components, or alternatively, may comprise one or more processing cores embodied in a single component (e.g., in a system-on-a-chip (SOC) configuration) and any processor-related support circuitry (e.g., bridging interfaces, etc.). Example processors may include various x86-based microprocessors available from the Intel Corporation including those in the Pentium, Xeon, Itanium, Celeron, Atom, Core i-series product families. Examples of support circuitry may include chipsets (e.g., Northbridge, Southbridge, etc. available from the Intel Corporation) configured to provide an interface through which processing module 104 may interact with other system components that may be operating at different speeds, on different buses, etc. within device 100. Processing module 104 may be configured to execute instructions in device 100. Instructions may include program code configured to cause processing module 104 to perform activities related to reading data, writing data, processing data, formulating data, converting data, transforming data, etc. Information (e.g., instructions, data, etc.) may be stored in memory module 106. Memory module 106 may comprise random access memory (RAM) and/or read-only memory (ROM) in a fixed or removable format. RAM may include memory configured to hold information during the operation of device 100 such as, for example, static RAM (SRAM) or Dynamic RAM (DRAM). ROM may include memories such as bios memory configured to provide instructions when device 100 activates, programmable memories such as electronic programmable ROMs, (EPROMS), Flash, etc. Other fixed and/or removable memory may include magnetic memories such as floppy disks, hard drives, etc., electronic memories such as solid state flash memory (e.g., eMMC, etc.), removable memory cards or sticks (e.g., uSD, USB, etc.), optical memories such as compact disc-based ROM (CD-ROM), etc. Power module 108 may include internal power sources (e.g., a battery) and/or external power sources (e.g., electromechanical or solar generator, power grid, etc.), and related circuitry configured to supply device 100 with the power needed to operate.

User interface module 110 may include circuitry configured to allow users to interact with device 100 such as, for example, various input mechanisms (e.g., microphones, switches, buttons, knobs, keyboards, speakers, touch-sensitive surfaces, one or more sensors configured to capture images and/or sense proximity, distance, motion, gestures, etc.) and output mechanisms (e.g., speakers, displays, lighted/flashing indicators, electromechanical components for vibration, motion, etc.). Communications interface module 112 may be configured to handle packet routing and other control functions for communication module 114, which may include resources configured to support wired and/or wireless communications. Wired communications may include serial and parallel wired mediums such as, for example, Ethernet, Universal Serial Bus (USB), Firewire, etc. Wireless communications may include, for example, close-proximity wireless mediums (e.g., radio frequency (RF) such as, for example, based on the Near Field Communications (NFC) standard, infrared (IR), optical character recognition (OCR), magnetic character sensing, etc.), short-range wireless mediums (e.g., Bluetooth, wireless local area networking (WLAN), Wi-Fi, etc.) and long range wireless mediums (e.g., cellular, satellite, etc.). In one embodiment, communications interface module 112 may be configured to prevent wireless communications that are active in communication module 114 from interfering with each other. In performing this function, communications interface module 112 may schedule activities for communication module 114 based on, for example, the relative priority of messages awaiting transmission.

Location Services module 118 may be configured to provide positioning functionality for device 100. For example, locations services module 118 may comprise one or more receivers configured to receive location information from an external source. One example of a receiver usable in this regard is a GPS receiver. Location services module 118 may further comprise, or may at least have access to, other resources in device 100 that may be usable for approximating device location, such as, for example, communication module 114 (e.g., for determining location using wireless network membership or via sensing proximate wireless devices and/or networks, network-based triangulation, etc.), as well as sensors configured to sense device orientation, motion, acceleration, etc. While communication module 114 and location services module 118 have been illustrated as separate from host 102, the disclosed configuration is merely for the sake of explanation herein. Some or all of the functionality associated with modules 114 or 118 may also be included within any of the various operational modules identified as making up host 102.

LPMM 116 may be a module in device 100 capable of operating both in the active mode and the power saving mode. For example, LPMM 116 may be configured to receive information from host 102 (e.g., from at least one location-aware application executing in host 102) and may further be configured to utilize the received information in performing location-related tasks when device 100 enters the power-saving mode. In at least one configuration, LPMM 116 may be hardware-based in that it may comprise at least a microcontroller and firmware integrated in a discrete IC or a SOC. The microcontroller may be configured to execute the firmware in LPMM 116 to support various functionality such as described further below with respect to FIG. 2.

Figure 2:
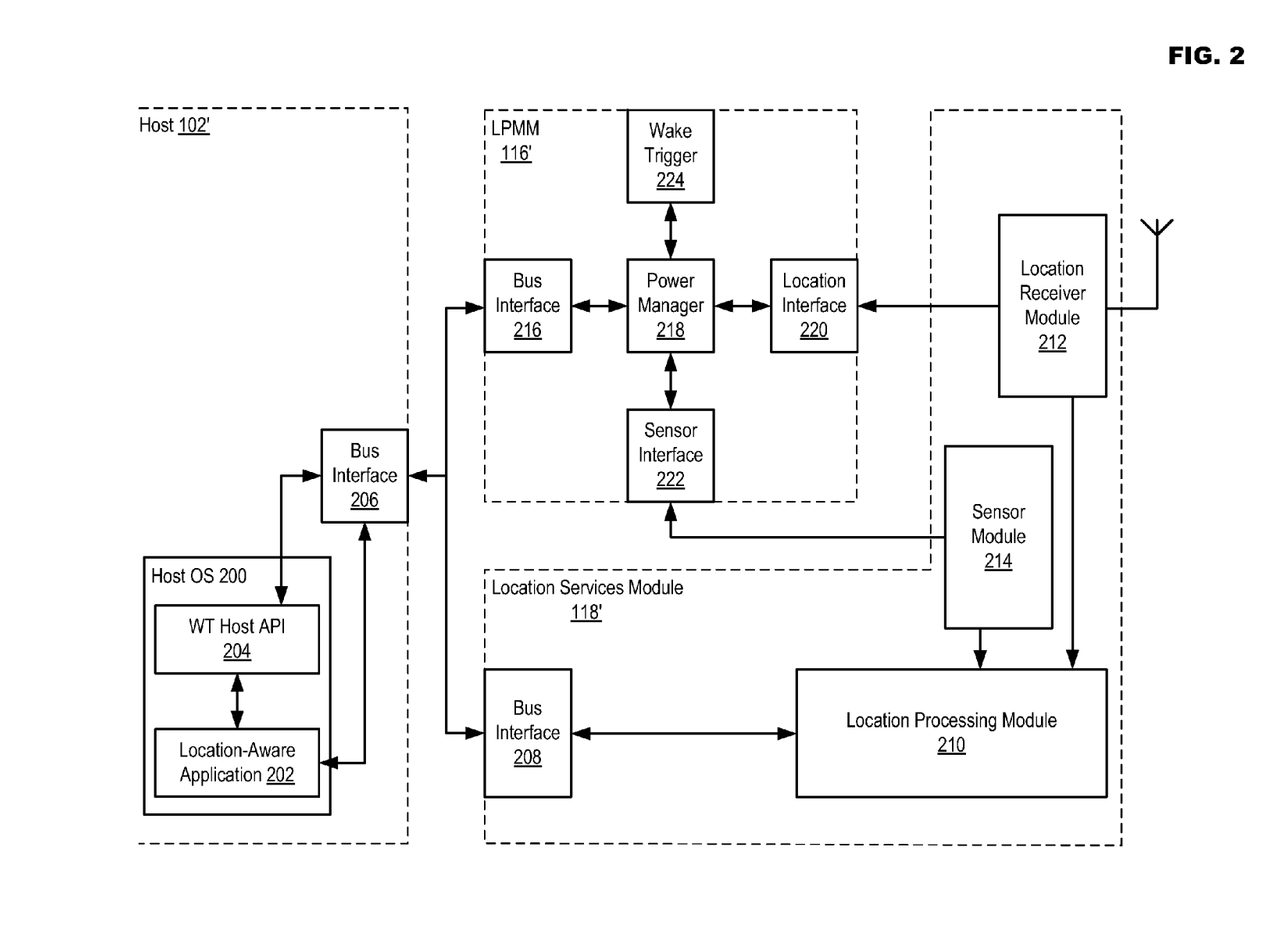
FIG. 2 illustrates example configurations for a host, lower power monitoring module and location services module in accordance with at least one embodiment of the present disclosure.

FIG. 2 illustrates example configurations for host 102', LPMM 116' and location services module 118' in accordance with at least one embodiment of the present disclosure. Host 102' may be running host operating system (OS) 200 in which various applications may execute. In one embodiment, at least one location-aware application 202 and a wake trigger (e.g., WT) host application program interface (API) 204 may be executing in host OS 200. Location-aware application 202 may be any application that employs positioning functionality (e.g., as provided by locations services module 118') in providing functionality to the user of device 100. For example, location-aware application 202 may be configured to determine locations of interest for the user of device 100. Locations of interest may include, for example, restaurants, shops, events, tourist attractions, or another place the user may desire to visit. In an alternative example of operation, Location-aware application 202 may also be able to locate items of interest to the user of device 100. For example, when the user desires to obtain an item, location-aware application 202 may be configured to provide information about the item (e.g., descriptions, specifications, reviews, cost, etc.) and may further determine local merchants having stock on the item (e.g., a type of merchant, for example a grocery store, or a particular merchant, for example a department store chain) and may determine locations for the local merchants having stock on the item. In one embodiment, location-aware application 202 may also determine at least one trigger limit. The trigger limit may indicate an area outside of which the current wake triggers are no longer applicable. For example, location-aware application 202 may determine locations where an item may be obtained. However, the locations may become irrelevant if device 100 travels away from these locations. In such an instance, the trigger limit may indicate that these locations are invalid and that new locations need to be determined that are closer to the current location of device 100.

Regardless of the functionality provided by location-aware application 202, the output of location-aware application 202 may be at least one location of interest. When device 100 is in the active mode, location-aware application 202 may utilize bus interface 206 to access location service module 118' directly. For example, location-aware application 202 may communicate with location processing module 210 via bus interfaces 206 and 208 to cause location processing module 210 to request device location information from location receiver module 212. While location receiver module 212 may be a GPS receiver configured to receive signals from one or more GPS satellites, it may also be possible for signal-based positioning to be performed based on terrestrial signal sources such as cell towers, nearby short-range wireless networks, etc. The device location information may then be provided to location processing module 210, which may determine the device location by, for example, triangulating the position of device 100 based on the location of the signal sources and the distance of device 100 from each of the signal sources. The device location may be further refined based on, for example, sensor information provided to location processing module 210 from sensor module 214. Location processing module 210 may then provide the device location to location-aware application 202 via bus interfaces 208 and 206. The above interaction may continue while device 100 remains in the active mode.

In instances where device 100 may be preparing to transition to the power saving mode, the at least one location of interest may be provided to WT Host API 204 that may communicate with at least wake trigger 224 in LPMM 116' via bus interfaces 206 and 216. LPMM 116' may include power manager 218, location interface 220, sensor interface 222 and wake trigger 224. Power manager 218 may be configured to control overall operation and may monitor the power usage of LPMM 116'. Location interface 220 may be configured to receive location information from location receiver module 212 and may determine a device location based on the location information. Sensor interface 222 may be configured to interact with sensor module 214, and may receive sensor information for use in, for example, determining a device displacement. In one embodiment, sensor interface 222 may comprise physical sensor micro drivers that may drive sensors without relying upon other device resources, which may help to further conserve power in the device 100. Wake trigger 224 may receive at least one wake trigger (and possibly a trigger limit), and may be configured to monitor the device location (e.g., received via location interface 220) and to cause device 100 to transition from the power saving mode to the active mode when it is determined that the device location corresponds to the at least one wake trigger or the trigger limit. The above elements of LPMM 116' may be further configured to request location information based on condition, which will be discussed further with respect to FIG. 3.

Figure 3:
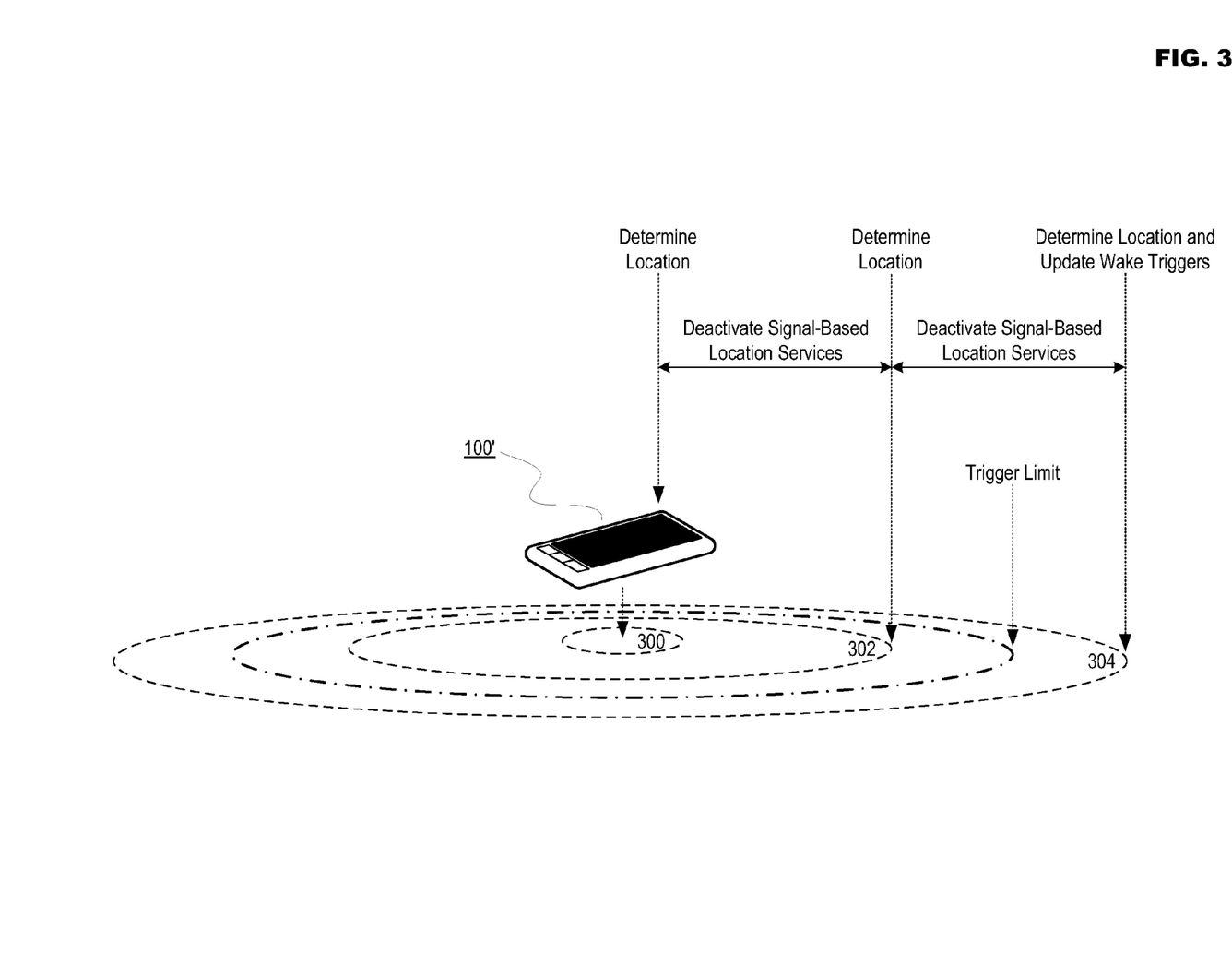
FIG. 3 illustrates an example of conditional location determination in accordance with at least one embodiment of the present disclosure.

FIG. 3 illustrates an example of conditional location determination in accordance with at least one embodiment of the present disclosure. While in the example disclosed in FIG. 3 device 100' has been shown as a mobile communication device, other types of devices may also be used in the same manner. In one embodiment, the device location may be provided to LPMM 116 by location services module 118 when certain conditions are realized. For example, LPMM 116 may be configured to request the device location when a location monitoring countdown timer expires. In this way, location services module 118 may be active at a reduced interval and power may be conserved in device 100'. Further power savings may be realized by using a location technique such as illustrated in FIG. 3. Device 100' may start at position 300. After providing the device location at position 300, location services module 118 may deactivate all signal-based location services (e.g., GPS, network sensing, etc.) and rely only on sensor information (e.g., motion, acceleration, etc.) in determining displacement for device 100'. The use of sensor information over signal-based location services may result in a significant power savings in device 100'.

The displacement of device 100' from position 300 may then be determined based on the sensor information. When the movement of device 100' corresponds to a threshold displacement (e.g., device 100' travels a certain distance from position 300 to arrive at position 302), location services module 118 may reinitiate signal-based location services (e.g., either automatically or in response to a request from LPMM 116). LPMM 116 may then receive the device location from location services module 118, and may determine whether the device location corresponds to a wake trigger or a trigger limit. Since in the example of FIG. 3 position 302 does not correspond to either a wake trigger or a trigger limit, location services module 118 may again deactivate signal-based location services until device 100' arrives at position 304 (e.g., a position corresponding to the threshold displacement measured from position 302). In the example of FIG. 3, when signal-based location services are again initiated at position 304 it may be determined that device 100' has arrived at (or has passed) the trigger limit, and as a result, the wake triggers in device 100' may be updated in accordance with the current location of device 100' (e.g., position 304).

Figure 4:
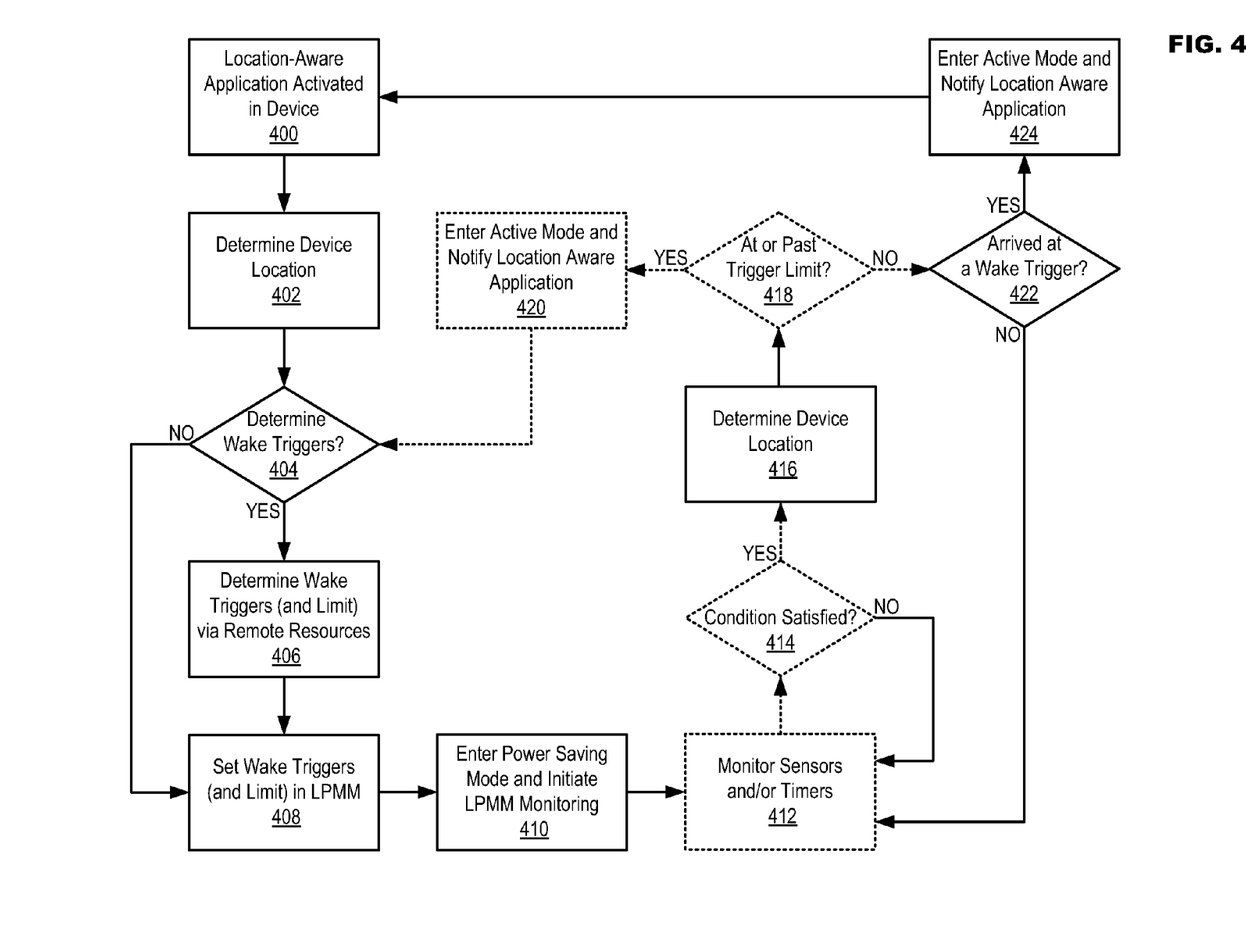
FIG. 4 illustrates a flowchart of example operations for power efficient location notification in accordance with at least one embodiment of the present disclosure.

FIG. 4 illustrates a flowchart of example operations for power efficient location notification in accordance with at least one embodiment of the present disclosure. In operation 400 at least one location aware application may be activated in a device that is operating in the active mode. The at least one location-aware application may then cause location services to determine the device location in operation 402. The device location may be determined via, for example, signal-based location services. A determination may then be made in operation 404 as to whether wake triggers need to be determined. For example, some location-aware applications may contain a predetermined set of wake triggers (e.g., store locations for a particular merchant), while other location-aware applications may be configured to determine wake triggers based on the device location (e.g., where the application is configured to identify locations where an item may be obtained within a certain distance from the device). If it is determined in operation 404 that wake triggers need to be determined, then in operation 406 the at least one location-aware application may cause the device to access remote resources (e.g., networked, Internet or "Cloud-based" servers via wireless communication) to determine wake triggers. For example, the at least one location-aware application may provide search parameters (e.g., type of establishment or type of item desired) along with the device location to the remote resources, which may then return at least one wake trigger. In one embodiment, the at least one wake trigger may be valid only within a certain range of the device location, and thus, a trigger limit may also be returned. If in operation 404 it is determined that the determination of wake triggers is not required, or alternatively, after determining the at least one wake trigger in operation 406, then in operation 408 the at least one wake trigger (and the trigger limit, if applicable) may be set in an LPMM.

In operation 410 the device may enter the power saving mode from the active mode and LPMM location monitoring may initiate. Operations 412 and 414 may be optional in that they may only be performed if the device is configured to provide device location updates based on a condition for additional power savings. If operations 412 and 414 were omitted then the "NO" determination in operation 422 would instead return to operation 416 to again determine device location instead of operation 412. In the disclosed embodiment, LPMM monitoring may include monitoring for a condition (e.g., for a location monitoring timer to expire, for the device displacement to correspond to a displacement threshold, etc.) in operation 412. The condition may continue to be monitored in operation 412 until in operation 414 a determination is made that the monitored conditions have been satisfied (e.g., the timer expired, the device displacement corresponds to the displacement threshold, etc.). In operation 416 the device location may be provided by location services in the device. Operations 418 and 420 may be optional in that they occur only if a trigger limit was set in operation 408. In operation 418 a determination may be made based on the device location received in operation 416 as to whether the device is at or past the trigger limit. If it is determined in operation 418 that the device is at or past the trigger limit, then in operation 420 the device may enter the active mode from the power saving mode and the at least one location-aware application may be notified of the device location. The notification may cause a return to operation 404 to reinitiate the wake trigger setting process in the device.

If in operation 418 it is determined that the device is not at or past the trigger limit, then in operation 422 a further determination may be made as to whether the device location received in operation 416 corresponds to the at least one wake trigger (e.g., if the device has arrived at a location of interest). If it is determined that the device location does not correspond to the at least one wake trigger, then LPMM monitoring may resume in operation 412. Otherwise, if it is determined that the device location does correspond to the at least one wake trigger, then in operation 424 the device may enter the active mode from the power saving mode, and the at least one location-aware application may be notified of the device location. The location-aware application may then, for example, provide functionality based on the device location, and may return to operation 400 in preparation for again setting wake triggers, LPMM monitoring, etc.

While FIG. 4 illustrates various operations according to an embodiment, it is to be understood that not all of the operations depicted in FIG. 4 are necessary for other embodiments. Indeed, it is fully contemplated herein that in other embodiments of the present disclosure, the operations depicted in FIG. 4, and/or other operations described herein, may be combined in a manner not specifically shown in any of the drawings, but still fully consistent with the present disclosure. Thus, claims directed to features and/or operations that are not exactly shown in one drawing are deemed within the scope and content of the present disclosure.

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage mediums. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry. Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), embedded multimedia cards (eMMCs), secure digital input/output (SDIO) cards, magnetic or optical cards, or any type of media suitable for storing electronic instructions. Other embodiments may be implemented as software modules executed by a programmable control device.

Thus, the present disclosure provides systems and methods for power efficient location notification. Before a device enters a power saving mode, a location-aware application in the device may provide at least one wake trigger (and a trigger limit) to a low power monitoring module (LPMM). In power saving mode, the LPMM receives device locations from a location service module and may determine when the device location corresponds to the at least one wake trigger or trigger limit. In one embodiment, device location may only be provided to the LPMM based on a condition (e.g., timer expiration or reaching a displacement threshold as measured by sensors in the device). When device location corresponds to the trigger limit, the LPMM may notify the device (e.g., cause a transition to an active power mode) so that the location-aware application can redetermine the at least one wake trigger. The device location corresponding to the at least wake trigger may also cause the LPMM to notify the device.

The following examples pertain to further embodiments. In one example embodiment there is provided a device. The device may include a host configured to operate in at least an active mode and a power saving mode, a location services module configured to determine device location, and a low power monitoring module configured to receive at least one wake trigger from the host, to receive the device location from the locations services module, and to cause the host to enter the active mode from the power saving mode when the low power monitoring module determines that the device location corresponds to the at least one wake trigger.

The above example device may be further configured, wherein the host is further configured to enter the power saving mode after providing the at least one wake trigger to the low power monitoring module.

The above example device may be further configured, wherein the host is further configured to provide a trigger limit to the low power monitoring module, the low power monitoring module further being configured to cause the host to enter the active mode from the power saving mode and to redetermine the at least one wake trigger when the low power monitoring module determines that the device location corresponds to the trigger limit.

The above example device may be further configured, wherein the host is further configured to execute at least one location-aware application when in the active mode, the at least one location-aware application being configured to provide the at least one wake trigger to the low power monitoring module. In this configuration, the example device may be further configured, wherein the at least one location-aware application is further configured to provide the device location to remote resources to determine the at least one wake trigger.

The above example device may be further configured, wherein the low power monitoring module is further configured to receive the device location based on the expiration of a location monitoring timer.

The above example device may be further configured, wherein the location services module is configured to determine device location based on at least one of a satellite-based positioning system or wireless network interaction. In this configuration, the example device may be further configured, wherein the location services module is further configured to sense device displacement based on at least one of orientation, motion or acceleration sensors. In this configuration, the example device may be further configured, wherein the low power monitoring module is further configured to receive the device displacement and to only receive the device location when the low power monitoring module determines that device displacement corresponds to a threshold distance.

The above example device may be further configured, wherein the low power monitoring module includes a microcontroller and firmware integrated in a discrete integrated circuit (IC) or a system-on-a-chip (SOC).

In another example embodiment there is provided a method, the method may include receiving at least one wake trigger from a host in a device, receiving a device location from a location services module in the device, and causing the host to transition from a low power mode to an active mode based on determining that the device location corresponds to the at least one wake trigger.

The above example method may be further configured, wherein the at least one wake trigger is received from at least one location aware application executing in the host when the host is in the active mode. In this configuration, the example method may be further configured, wherein the at least one wake trigger corresponds to a location of interest, the location of interest being identified by the at least one location aware application. In this configuration, the example method may be further configured, wherein the at least one wake trigger corresponds to a location of an item desired by the user of the device, the location of the item being determined based on information from a remote resource accessed by the at least one location aware application.

The above example method may further comprise receiving a trigger limit from the host in the device, and causing the host to transition from a low power mode to an active mode and to redetermine the at least one wake trigger based on determining that the device location corresponds to the trigger limit.

The above example method may be further configured, wherein the device location is received based on the expiration of a location monitoring timer.

The above example method may be further configured, wherein the device location is based on at least one of a satellite-based positioning system or wireless network interaction. In this configuration, the example method may further comprise receiving a device displacement from the location services module in the device, determining whether the device displacement corresponds to a threshold distance, and receiving the device location if the device displacement corresponds to the threshold distance. In this configuration, the example method may be further configured, wherein device displacement is based on at least one of orientation, motion or acceleration sensors in the device.

In another example embodiment there is provided a system including at least a device, the system being arranged to perform any of the above example methods.

In another example embodiment there is provided a chipset arranged to perform any of the above example methods.

In another example embodiment there is provided at least one machine readable medium comprising a plurality of instructions that, in response to be being executed on a computing device, cause the computing device to carry out any of the above example methods.

In another example embodiment there is provided a device comprising at least a host, a low power monitoring module and a location services module, the device being arranged to perform any of the above example methods.

In another example embodiment there is provided a system comprising at least one machine-readable storage medium having stored thereon, individually or in combination, instructions that when executed by one or more processors result in the system performing any of the above example methods.

In another example embodiment there is provided a device. The device may include a host configured to operate in at least an active mode and a power saving mode, a location services module configured to determine device location, and a low power monitoring module configured to receive at least one wake trigger from the host, to receive the device location from the locations services module, and to cause the host to enter the active mode from the power saving mode when the low power monitoring module determines that the device location corresponds to the at least one wake trigger.

The above example device may be further configured, wherein the host is further configured to provide a trigger limit to the low power monitoring module, the low power monitoring module being further configured to cause the host to enter the active mode from the power saving mode and to redetermine the at least one wake trigger when the low power monitoring module determines that the device location corresponds to the trigger limit.

The above example device may be further configured, wherein the host is further configured to execute at least one location-aware application when in the active mode, the at least one location-aware application being configured to provide the at least one wake trigger to the low power monitoring module. In this configuration, the example device may be further configured, wherein the at least one location-aware application is further configured to provide the device location to remote resources to determine the at least one wake trigger.

The above example device may be further configured, wherein the location services module is configured to determine device location based on at least one of a satellite-based positioning system or wireless network interaction. In this configuration, the example device may be further configured, wherein the location services module is further configured to sense device displacement based on at least one of orientation, motion or acceleration sensors. In this configuration, the example device may be further configured, wherein the low power monitoring module is further configured to receive the device displacement and to only receive the device location when the low power monitoring module determines that device displacement corresponds to a threshold distance.

In another example embodiment there is provided a method. The method may include receiving at least one wake trigger from a host in a device, receiving a device location from a location services module in the device, and causing the host to transition from a low power mode to an active mode based on determining that the device location corresponds to the at least one wake trigger.

The above example method may be further configured, wherein the at least one wake trigger is received from at least one location aware application executing in the host when the host is in the active mode.

The above example method may further comprise receiving a trigger limit from the host in the device, and causing the host to transition from a low power mode to an active mode and to redetermine the at least one wake trigger based on determining that the device location corresponds to the trigger limit.

The above example method may be further configured, wherein the device location is based on at least one of a satellite-based positioning system or wireless network interaction. In this configuration, the example method may further comprise receiving a device displacement from the location services module in the device, the device displacement being based on at least one of orientation, motion or acceleration sensors in the device, determining whether the device displacement corresponds to a threshold distance, and receiving the device location if the device displacement corresponds to the threshold distance.

In another example embodiment there is provided a system including at least a device, the system being arranged to perform any of the above example methods.

In another example embodiment there is provided a chipset arranged to perform any of the above example methods.

In another example embodiment there is provided at least one machine readable medium comprising a plurality of instructions that, in response to be being executed on a computing device, cause the computing device to carry out any of the above example methods.

In another example embodiment there is provided a device. The device may include a host configured to operate in at least an active mode and a power saving mode, a location services module configured to determine device location, and a low power monitoring module configured to receive at least one wake trigger from the host, to receive the device location from the locations services module, and to cause the host to enter the active mode from the power saving mode when the low power monitoring module determines that the device location corresponds to the at least one wake trigger.

The above example device may be further configured, wherein the host is further configured to enter the power saving mode after providing the at least one wake trigger to the low power monitoring module.

The above example device may be further configured, wherein the host is further configured to provide a trigger limit to the low power monitoring module, the low power monitoring module further being configured to cause the host to enter the active mode from the power saving mode and to redetermine the at least one wake trigger when the low power monitoring module determines that the device location corresponds to the trigger limit.

The above example device may be further configured, wherein the host is further configured to execute at least one location-aware application when in the active mode, the at least one location-aware application being configured to provide the at least one wake trigger to the low power monitoring module. In this configuration, the example device may be further configured, wherein the at least one location-aware application is further configured to provide the device location to remote resources to determine the at least one wake trigger.

The above example device may be further configured, wherein the low power monitoring module is further configured to receive the device location based on the expiration of a location monitoring timer.

The above example device may be further configured, wherein the location services module is configured to determine device location based on at least one of a satellite-based positioning system or wireless network interaction. In this configuration, the example device may be further configured, wherein the location services module is further configured to sense device displacement based on at least one of orientation, motion or acceleration sensors. In this configuration, the example device may be further configured, wherein the low power monitoring module is further configured to receive the device displacement and to only receive the device location when the low power monitoring module determines that device displacement corresponds to a threshold distance.

The above example device may be further configured, wherein the low power monitoring module includes a microcontroller and firmware integrated in a discrete integrated circuit (IC) or a system-on-a-chip (SOC).

In another example embodiment there is provided a method, the method may include receiving at least one wake trigger from a host in a device, receiving a device location from a location services module in the device, and causing the host to transition from a low power mode to an active mode based on determining that the device location corresponds to the at least one wake trigger.

The above example method may be further configured, wherein the at least one wake trigger is received from at least one location aware application executing in the host when the host is in the active mode. In this configuration, the example method may be further configured, wherein the at least one wake trigger corresponds to a location of interest, the location of interest being identified by the at least one location aware application. In this configuration, the example method may be further configured, wherein the at least one wake trigger corresponds to a location of an item desired by the user of the device, the location of the item being determined based on information from a remote resource accessed by the at least one location aware application.

The above example method may further comprise receiving a trigger limit from the host in the device, and causing the host to transition from a low power mode to an active mode and to redetermine the at least one wake trigger based on determining that the device location corresponds to the trigger limit.

The above example method may be further configured, wherein the device location is received based on the expiration of a location monitoring timer.

The above example method may be further configured, wherein the device location is based on at least one of a satellite-based positioning system or wireless network interaction. In this configuration, the example method may further comprise receiving a device displacement from the location services module in the device, determining whether the device displacement corresponds to a threshold distance, and receiving the device location if the device displacement corresponds to the threshold distance. In this configuration, the example method may be further configured, wherein device displacement is based on at least one of orientation, motion or acceleration sensors in the device.

In another example embodiment there is provided a system. The system may include means for receiving at least one wake trigger from a host in a device, means for receiving a device location from a location services module in the device, and means for causing the host to transition from a low power mode to an active mode based on determining that the device location corresponds to the at least one wake trigger.

The above example system may be further configured, wherein the at least one wake trigger is received from at least one location aware application executing in the host when the host is in the active mode. In this configuration, the example system may be further configured, wherein the at least one wake trigger corresponds to a location of interest, the location of interest being identified by the at least one location aware application. In this configuration, the example system may be further configured, wherein the at least one wake trigger corresponds to a location of an item desired by the user of the device, the location of the item being determined based on information from a remote resource accessed by the at least one location aware application.

The above example system may further comprise means for receiving a trigger limit from the host in the device, and means for causing the host to transition from a low power mode to an active mode and to redetermine the at least one wake trigger based on determining that the device location corresponds to the trigger limit.

The above example system may be further configured, wherein the device location is received based on the expiration of a location monitoring timer.

The above example system may be further configured, wherein the device location is based on at least one of a satellite-based positioning system or wireless network interaction. In this configuration, the example system may further comprise means for receiving a device displacement from the location services module in the device, means for determining whether the device displacement corresponds to a threshold distance, and means for receiving the device location if the device displacement corresponds to the threshold distance. In this configuration, the example system may be further configured, wherein device displacement is based on at least one of orientation, motion or acceleration sensors in the device.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed:

1. A device, comprising:
 a host configured to operate in at least an active mode and a power saving mode;
 a location services module: and
 a low power monitoring module; wherein:
 the location services module is configured to:
  determine a first device location based at least in part on signal-based location services and provide the first device location to the low power monitoring module;
  deactivate said signal-based location services after providing said first device location to the low power monitoring module;
  sense a displacement of said device from said first device location based on at least one of orientation, motion, or acceleration sensors while said signal-based locations services are deactivated;
  reactivate said signal-based location services and determine a second device location with said signal-based location services when said displacement from said first location meets or exceeds a threshold distance; and
 provide said second device location to said low power monitoring module; and
 the low power monitoring module is configured to receive at least one wake trigger from the host, to receive at least one of the first device location and second device location from the location services module, and to cause the host to enter the active mode from the power saving mode when the low power monitoring module determines that at least one of the first device location and the second device location corresponds to the at least one wake trigger.

2. The device of claim 1, wherein the host is further configured to enter the power saving mode after providing the at least one wake trigger to the low power monitoring module.

3. The device of claim 1, wherein the host is further configured to provide a trigger limit to the low power monitoring module, the low power monitoring module further being configured to cause the host to enter the active mode from the power saving mode and to redetermine the at least one wake trigger when the low power monitoring module determines that at least one of the first device location and the second device location corresponds to the trigger limit.

4. The device of claim 1, wherein the host is further configured to execute at least one location-aware application when in the active mode, the at least one location-aware application being configured to provide the at least one wake trigger to the low power monitoring module.

5. The device of claim 4, wherein the at least one location-aware application is further configured to provide at least one of the first device location and the second device location to remote resources to determine the at least one wake trigger.

6. The device of claim 1, wherein the low power monitoring module is further configured to receive the device location based on the expiration of a location monitoring timer.

7. The device of claim 1, wherein the signal-based location services comprise at least one of a satellite-based positioning system and interaction with a wireless network.

8. The device of claim 1, wherein the location services module is configured to reactivate said signal-based location services in response to a request from the low power monitoring module.

9. The device of claim 8, wherein the low power monitoring module is further configured to receive the device displacement when said signal-based locations services are deactivated, and to only receive the second device location when the low power monitoring module determines that said displacement meets or exceeds said threshold distance.

10. The device of claim 1, wherein the low power monitoring module includes a microcontroller and firmware integrated in a discrete integrated circuit (IC) or a system-on-a-chip (SOC).

11. A method, comprising:
receiving at least one wake trigger from a host in a device;
determining, with a location services module in the device, a first location of the device with signal-based location services;
with a low power monitoring module in the device, receiving the first device location from the location services module;
deactivating the signal-based location services with said location services module after said first location has been determined;
determining whether the first device location corresponds to the at least one wake trigger;
when the first device location corresponds to the at least one wake trigger:
causing the host to transition from a low power mode to an active mode;
when the first device location does not correspond to the at least one wake up trigger:
sensing a displacement of said device from said first location based on at least one of orientation, motion, or acceleration sensors while said signal-based location services are deactivated;
with said location services module, reactivating said signal-based location services and determining a second location of said device with said signal-based location services when the displacement of said device meets or exceeds a threshold distance;
with the low power monitoring module, receiving the second device location from the low power monitoring module;
causing the host to transition from a low power mode to an active mode when the second device location corresponds to the at least one wake trigger.

12. The method of claim 11, wherein the at least one wake trigger is received from at least one location aware application executing in the host when the host is in the active mode.

13. The method of claim 12, wherein the at least one wake trigger corresponds to a location of interest, the location of interest being identified by the at least one location aware application.

14. The method of claim 12, wherein the at least one wake trigger corresponds to a location of an item desired by the user of the device, the location of the item being determined based on information from a remote resource accessed by the at least one location aware application.

15. The method of claim 11, further comprising:
receiving a trigger limit from the host in the device; and
causing the host to transition from a low power mode to an active mode and to redetermine the at least one wake trigger based on determining that the device location corresponds to the trigger limit.

16. The method of claim 11, wherein at least one of the first device location and second device location is received based on the expiration of a location monitoring timer.

17. The method of claim 11, wherein the signal-based location services comprise at least one of a satellite-based positioning system interaction with a wireless network.

18. The method of claim 11, wherein said signal-based location services are reactivated by said location services module in response to a request from said low power monitoring module.

19. A system comprising at least one non-transitory machine-readable storage medium having stored thereon, individually or in combination, instructions that when executed by one or more processors result in the following operations comprising:
receiving at least one wake trigger from a host in a device;
determining, with a location services module in the device, a first location of the device with signal-based location services;
with a low power monitoring module in the device, receiving the first device location from the location services module;
deactivating the signal-based location services with said location services module after said first location has been determined;
determining whether the first device location corresponds to the at least one wake trigger;
when the first device location corresponds to the at least one wake trigger:
causing the host to transition from a low power mode to an active mode;
when the first device location does not correspond to the at least one wake up trigger:
sensing a displacement of said device from said first location based on at least one of orientation, motion, or acceleration sensors while said signal-based location services are deactivated;

with said location services module, reactivating said signal-based location services and determining a second location of said device with said signal-based location services when the displacement of said device meets or exceeds a threshold distance;

with the low power monitoring module, receiving the second device location from the low power monitoring module;

causing the host to transition from a low power mode to an active mode when the second device location corresponds to the at least one wake trigger.

20. The system of claim 19, wherein the at least one wake trigger is received from at least one location aware application executing in the host when the host is in the active mode.

21. The system of claim 20, wherein the at least one wake trigger corresponds to a location of interest, the location of interest being identified by the at least one location aware application.

22. The system of claim 20, wherein the at least one wake trigger corresponds to a location of an item desired by the user of the device, the location of the item being determined based on information from a remote resource accessed by the at least one location aware application.

23. The system of claim 19, further comprising instructions that when executed by one or more processors result in the following operations comprising:

receiving a trigger limit from the host in the device; and causing the host to transition from a low power mode to an active mode and to redetermine the at least one wake trigger based on determining that the device location corresponds to the trigger limit.

24. The system of claim 19, wherein at least one of the first device location and second device location is received based on the expiration of a location monitoring timer.

25. The system of claim 19, wherein the signal-based location services comprise at least one of a satellite-based positioning system interaction with a wireless network.

26. The system of claim 25, further comprising instructions that when executed by one or more processors result in the following operations comprising:

reactivating said signal-based location services by said location services module in response to a request from said low power management module.

* * * * *